United States Patent [19]

Griss, deceased et al.

[11] Patent Number: 4,886,812
[45] Date of Patent: Dec. 12, 1989

[54] TETRAHYDRO-BENZTHIAZOLES, THE PREPARATION THEREOF AND THEIR USE AS INTERMEDIATE PRODUCTS OR AS PHARMACEUTICALS

[75] Inventors: Gerhart Griss, deceased, late of Biberach, by Elisabeth Griss, legal representative; Claus Schneider, Ingelheim am Rhein; Rudolf Hurnaus, Biberach, all of Fed. Rep. of Germany; Walter Kobinger; Ludwig Pichler, both of Vienna, Austria; Rudolf Bauer, Wiesbaden, Fed. Rep. of Germany; Joachim Mierau, Mainz, Fed. Rep. of Germany; Dieter Hinzen, Zornheim, Fed. Rep. of Germany; Gunter Schingnitz, Bad Kreuznach, Fed. Rep. of Germany

[73] Assignee: Dr. Karl Thomae GmbH, Biberach an der Riss, Fed. Rep. of Germany

[21] Appl. No.: 256,671

[22] Filed: Oct. 12, 1988

Related U.S. Application Data

[62] Division of Ser. No. 124,197, Nov. 23, 1987, Pat. No. 4,843,086, which is a division of Ser. No. 810,947, Dec. 19, 1985, Pat. No. 4,731,374.

[30] Foreign Application Priority Data

Dec. 22, 1984 [DE] Fed. Rep. of Germany ..... 34470751
Mar. 13, 1985 [DE] Fed. Rep. of Germany ....... 3508947

[51] Int. Cl.⁴ ................ C07D 277/82; A01K 31/425
[52] U.S. Cl. ..................................... 514/321; 514/367; 548/161; 548/163; 548/164; 546/198; 540/603; 544/135
[58] Field of Search ............... 548/161, 163, 164; 546/198; 540/603; 544/135; 514/321, 367

[56] References Cited

U.S. PATENT DOCUMENTS 4,337,343 6/1982 Maillard et al. ............... 548/152

FOREIGN PATENT DOCUMENTS 21940 1/1981 European Pat. Off. ........... 548/161
0044443 1/1982 European Pat. Off. ........... 548/161
207696 8/1986 European Pat. Off. ........... 548/161
812512 4/1959 United Kingdom ............... 548/161

*Primary Examiner*—Robert Gerstl
*Attorney, Agent, or Firm*—David E. Frankhouser; Alan R. Stempel; Mary-Ellen M. Timbers

[57] ABSTRACT

This invention relates to new tetrahydrobenzthiazoles of general formula

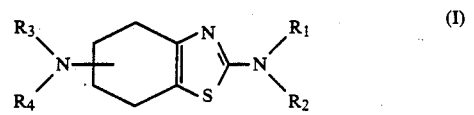

wherein $R_1$ represents a hydrogen atom, an alkyl group, an alkenyl or alkynyl group, an alkanoyl group, a phenyl alkyl or phenyl alkanoyl group, while the above mentioned phenyl nucleic may each be substituted by 1 or 2 halogen atoms, $R_2$ represents a hydrogen atom or an alkyl group, $R_3$ represents a hydrogen atom, an alkyl group a cycloalkyl group, an alkenyl or alkynyl group, an alkanoyl group, a phenyl alkyl or phenyl alkanoyl group, while the phenyl nucleus may be substituted by fluorine, chlorine or bromine atoms, $R_4$ represents a hydrogen atom, an alkyl group, an alkyl or alkenyl group, or $R_3$ and $R_4$ together with the nitrogen atom between them represent a pyrrolidino, piperidino, hexamethyleneimino or morpholino group, the enantiomers and the acid addition salts thereof.

The compounds of general formula I above in which one of the groups $R_1$ or $R_3$ or both groups $R_1$ and $R_3$ represent an acyl group are valuable intermediate products for preparing the other compounds of general formula I which have valuable pharmacological properties. The new compounds may be prepared using methods known per se.

10 Claims, No Drawings

TETRAHYDRO-BENZTHIAZOLES, THE PREPARATION THEREOF AND THEIR USE AS INTERMEDIATE PRODUCTS OR AS PHARMACEUTICALS

This is a division of application Ser. No. 124,197, filed Nov. 23, 1987, now U.S. Pat. No. 4,843,086, which is a division of Ser. No. 810,947, filed Dec. 19, 1985, now U.S. Pat. No. 4,731,374.

This invention relates to new tetrahydrobenzthiazoles of general formula

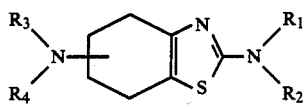 (I)

the enantiomers and acid addition salts thereof, particularly the pharmaceutically acceptable acid addition salts thereof with inorganic or organic acids, and processes for preparing them.

Compounds of general formula I wherein $R_1$ or $R_3$ or both groups $R_1$ and $R_3$ represent an acyl group are valuable intermediate products for preparing other compounds of general formula I which have valuable pharmacological properties, particularly an effect on the central nervous system and/or the circulation.

In general formula I above $R_1$ represents a hydrogen atom, an alkyl group having 1 to 6 carbon atoms, an alkenyl or alkynyl group each having 3 to 6 carbon atoms, an alkanoyl group having 1 to 6 carbon atoms, a phenyl alkyl or phenyl alkanoyl group having 1 to 3 carbon atoms in the alkyl part, whilst the above mentioned phenyl nuclei may be substituted by 1 or 2 halogen atoms, $R_2$ represents a hydrogen atom or an alkyl group with 1 to 4 carbon atoms, $R_3$ represents a hydrogen atom, an alkyl group with 1 to 7 carbon atoms, a cycloalkyl group having 3 to 7 carbon atoms, an alkenyl or alkynyl group having 3 to 6 carbon atoms, an alkanoyl group having 1 to 7 carbon atoms, a phenyl alkyl or phenyl alkanoyl group having 1 to 3 carbon atoms in the alkyl part, whilst the phenyl nucleus may be substituted by fluorine, chlorine or bromine atoms, $R_4$ represents a hydrogen atom, an alkyl group with 1 to 4 carbon atoms, an alkenyl or alkynyl group having 3 to 6 carbon atoms or $R_3$ and $R_4$ together with the nitrogen atom between them represent a pyrrolidino, piperidino, hexamethyleneimino or morpholino group.

Preferred compounds of general formula I above are those wherein the group

is in the 5 or 6-position.

As examples of the definitions of the groups

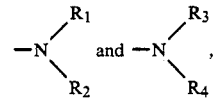

the

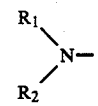

group represents an amino, methylamino, ethylamino, n-propylamino, isopropylamino, n-butylamino, isobutylamino, tert.butylamino, n-pentylamino, isoamylamino, n-hexylamino, dimethylamino, diethylamino, di-n-propylamino, di-n-butylamino, methyl-ethylamino, methyl-n-propylamino, methylisopropylamino, ethyl-isopropylamino, allylamino, buten-2-ylamino, hexen-2-ylamino, N-methylallylamino, N-ethyl-allylamino, N-n-propylallylamino, N-n-butyl-allylamino, propargylamino, N-methyl-propargylamino, N-n-propyl-propargylamino, formylamino, acetylamino, propionylamino, butanoylamino, hexanoylamino, N-methyl-acetylamino, N-allyl-acetylamino, N-propargyl-acetylamino, benzylamino, N-methyl-benzylamino, 2-chloro-benzylamino, 4-chloro-benzylamino, 4-fluoro-benzylamino, 3,4-dichloro-benzylamino, 1-phenylethylamino, 2-phenylethylamino, 3-phenyl-n-propylamino, benzoylamino phenacetylamino or 2-phenylpropionylamino group and the group

may represent an amino, methylamino, ethylamino, n-propylamino, isopropylamino, n-butylamino, isobutylamino, tert.butylamino, n-pentylamino, isoamylamino, n-hexylamino, n-heptylamino, dimethylamino, diethylamino, di-n-propylamino, Di-n-butylamino, methyl-ethylamino, methyl-n-propylamino, methyl-isopropylamino, ethyl-isopropylamino, allylamino, buten-2-ylamino, hexen-2-ylamino, diallylamino, N-methyl-allylamino, N-ethyl-allylamino, N-n-propyl-allylamino, N-n-butyl-allylamino, propargylamino, butin-2-ylamino, hexin-2-ylamino, dipropargylamino, N-methyl-propargylamino, N-ethyl-propargylamino, cyclopropylamino, cyclobutylamino, cyclopentylamino, cyclohexylamino, cycloheptylamino, N-methyl cyclohexylamino, N-ethyl-cyclohexylamino, formylamino, acetylamino, propionylamino, butanoylamino, pentanoylamino, hexanoylamino, heptanoylamino, N-methyl-acetylamino, N-ethyl- acetylamino, N-n-propyl-acetylamino, N-allyl-acetylamino, benzoylamino, fluorobenzoylamino, chlorobenzoylamino, bromobenzoylamino, phenylacetamino, 2-phenylpropionylamino, N-methyl-benzoylamino, N-ethyl-chlorobenzoylamino, Dichlorobenzoylamino, N-cyclohexyl-acetylamino, benzylamino, chlorobenzylamino, bromobenzylamino, 1-phenylethylamino, 2-phenylethylamino, 2-phenyl-n-propylamino, 3-phenyl-n-propylamino, N-methyl-benzylamino, N-ethyl-benzylamino, N-ethyl-chlorobenzylamino, N-ethyl-2-phenylethylamino, N-acetyl-benzylamino, N-acetyl-chlorobenzylamino, N-allyl-benzylamino, N-allyl-chlorobenzylamino, pyrrolidino, piperidino, hexamethyleneimino or morpholino group.

Particularly preferred compounds of general formula I are, however, the compounds of general formula Ia

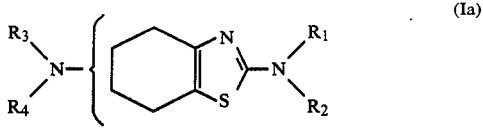

wherein $R_1$ represents a hydrogen atom, an alkyl group having 1 to 3 carbon atoms, an allyl, benzyl, 2-chloro-benzyl, 4-chloro-benzyl, 3,4-dichloro-benzyl or phenylethyl group, $R_2$ represents a hydrogen atom, a methyl or ethyl group, $R_3$ represents a hydrogen atom, an alkyl group with 1 to 6 carbon atoms, an allyl, propargyl, benzyl, chlorobenzyl, phenylethyl, cyclopentyl or cyclohexyl group, $R_4$ represents a hydrogen atom, an alkyl group having 1 to 3 carbon atoms or an allyl group or $R_3$ and $R_4$ together with the nitrogen atom between them represent a pyrrolidino, piperidino, hexamethyleneimino or morpholino group, but particularly the compounds wherein the group

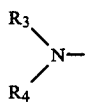

is in the 6-position, and the acid addition salts thereof, particularly the pharmaceutically acceptable acid addition salts.

According to the invention the new compounds are obtained by the following methods:

(a) Reacting a cyclohexanone of general formula

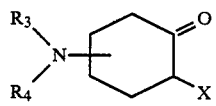

wherein $R_3$ and $R_4$ are as hereinbefore defined and

X represents a nucleophilically exchangeable group such as a halogen atom, e.g. a chlorine or bromine atom, with a thiourea of general formula

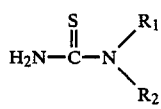

wherein $R_1$ and $R_2$ are as hereinbefore defined.

The reaction is carried out in a melt or in a solvent or mixture of solvents such as water, ethanol, water/ethanol, pyridine, dioxan, dioxan/water, glacial acetic acid, tetrahydrofuran or dimethylformamide, conveniently at temperatures of between 0° and 150° C., preferably at temperatures of between 20° and 100° C. and optionally in the presence of a base, e.g. sodium hydroxide solution, sodium acetate, pyridine, triethylamine or N-ethyl-diisopropylamine. The compounds of general formula II used as starting materials need not be isolated.

(b) Reacting a compound of general formula

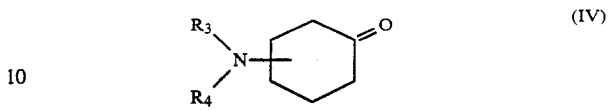

wherein $R_3$ and $R_4$ are as hereinbefore defined, with a formamidine disulfide of general formula

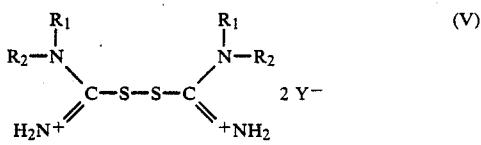

wherein $R_1$ and $R_2$ are as hereinbefore defined and $Y^-$ represents an anion of an inorganic or organic acid.

The reaction is preferably carried out in a melt or in a high-boiling solvent such as glycol, dimethylformamide, diphenylether or dichlorobenzene, conveniently at temperatures of between 25° and 200° C., preferably at temperatures of between 70° and 150° C.

(c) In order to prepare compounds of general formula I wherein at least one of the groups $R_1$, $R_2$, $R_3$ or $R_4$ represents a hydrogen atom;

splitting off a protecting group from a compound of general formula

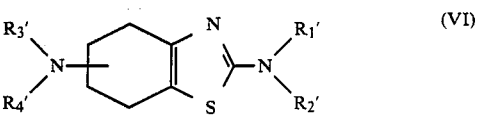

wherein at least one of the groups $R_1'$, $R_2'$, $R_3'$ or $R_4'$ represents a protecting group for an amino group such as an acyl or alkoxycarbonyl group, e.g. an acetyl, propionyl, methoxycarbonyl or ethoxycarbonyl group, or $R_1'$ and $R_2'$ or $R_3'$ and $R_4'$ together with the nitrogen atom between them represent an imido group, e.g. the phthalimido group, and The other groups $R_1$, $R_2$, $R_3$ or $R_4$ have the meanings given for $R_1$ to $R_4$ hereinbefore, with the exception of the acyl groups mentioned hereinbefore.

The splitting off of a protecting group is preferably carried out by hydrolysis in the presence of a base such as sodium hydroxide solution or potassium hydroxide solution or in the presence of an acid such as hydrochloric or sulphuric acid in an aqueous solvent such as water/ethanol, water/dioxan or water/tetrahydrofuran at temperatures of between 50° and 150° C., preferably at the boiling temperature of the reaction mixture. An imido group such as the phthalimido group used as a protecting group is preferably split off with hydrazine in a solvent such as water, water/ethanol or water/dioxan at the boiling temperature of the solvent used.

(d) In order to prepare compounds of general formula I wherein at least one of the groups $R_1$, $R_2$, $R_3$ or $R_4$ represents one of the above-mentioned alkyl, or phenylalkyl group:

Reduction of a compound of general formula

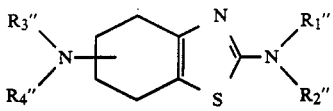
VII wherein at least one of the groups $R_1''$, $R_2''$, $R_3''$ or $R_4''$ represents one of the acyl or phenylacyl groups mentioned hereinbefore and the other groups have the meanings given for $R_1$, $R_2$, $R_3$ and $R_4$ hereinbefore, with a metal hydride in a solvent.

The reduction is carried out in a suitable solvent such as diethylether, tetrahydrofuran, glycoldimethylether or dioxan with a metal hydride, e.g. with a complex metal hydride such as lithium aluminium hydride, at temperatures of between 0° and 100° C., but preferably at temperatures of between 20° and 80° C.

In order to prepare compounds of general formula I wherein one of the groups $R_3$ or $R_4$ represents one of the acyl groups mentioned hereinbefore, it is particularly advantageous to carry out the reaction with lithium aluminium hydride at temperatures of between 0° and 30° C., preferably at ambient temperature.

(e) In order to prepare compounds of general formula I wherein at least one of the groups $R_1$, $R_2$, $R_3$ or $R_4$ represents one of the alkyl, cycloalkyl, alkenyl, alkynyl or phenylalkyl groups mentioned hereinbefore:

Reacting a compound of general formula

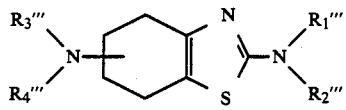
(VIII)

wherein at least one of the groups $R_1'''$, $R_2'''$, $R_3'''$ or $R_4'''$ represents a hydrogen atom and the other groups $R_1'''$, $R_2'''$, $R_3'''$ or $R_4'''$ have the meanings given for $R_1$ to $R_4$ hereinbefore, with a compound of general formula $$R_5-Z \qquad (IX)$$

wherein $R_5$ represents one of the alkyl, cycloalkyl, alkenyl, alkinyl or phenylalkyl groups mentioned for $R_1$ to $R_4$ hereinbefore and Z represents a nucleophili- cally exchangeable group such as a halogen atom or a sulfonic acid group, e.g. a chlorine, bromine or iodine atom, a methoxysulfonyloxy or p- toluenesulfonyloxy group, or Z together with an adjacent hydrogen of the group $R_5$ represents an oxygen.

The reaction is carried out in a solvent such as water, methanol, ethanol, tetrahydrofuran, dioxan, acetone, acetonitrile or dimethylsulfoxide with an alkylating agent such as methyliodide, dimethylsulfate, ethylbromide, diethylsulfate, allyliodide, benzylbromide, 2-phenylethylbromide or methyl-p- toluenesulfonate, optionally in the presence of a base such as sodium hydroxide solution, potassium carbonate, sodium hydride, potassium-tert.butoxide or triethylamine, conveniently at temperatures of between −10° and 50° C., but preferably at temperatures of between 0° and 30° C. However, the reaction may also be carried out without a solvent.

Alkylation of the nitrogen atom may also be effected using formaldehyde/formic acid at elevated temperatures, e.g. at the boiling temperature of the reaction mixture, or with a corresponding carbonyl compound and a complex metal hydride such as sodiumborohydride or sodiumcyanoborohydride in a solvent such as water/methanol, ethanol, ethanol/water, dimethylformamide or tetrahydrofuran at temperatures of between 0° and 50° C., but preferably at ambient temperature.

If according to the invention a compound of general formula I is obtained wherein at least one of the groups $R_1$, $R_2$, $R_3$ or $R_4$ represents a hydrogen atom, this may be converted by corresponding acylation into a corresponding compound of general formula I wherein at least one of the groups $R_1$, $R_2$, $R_3$ or $R_4$ represents one of the acyl groups mentioned herein before.

The subsequent acylation is appropriately carried out in a solvent such as methylene chloride, chloroform, carbontetrachloride, ether, tetrahydrofuran, dioxan, glacial acetic acid, benzene, toluene, acetonitrile or dimethylformamide, optionally in the presence of an acid-activating agent or a dehydrating agent, e.g. in the presence of ethyl chloroformate, thionylchloride, N,N-dicyclohexylcarbodiimide, N,N'-dicyclohexyl carbodiimide/N-hydroxysuccinimide, N,N'-carbonyldiimidazole or N,N'-thionyldiimidazole or triphenylphosphine/carbontetrachloride, or an agent which activates the amino group, e.g. phosphorus trichloride, and optionally in the presence of an inorganic base such as sodium carbonate or a tertiary organic base such as triethylamine or pyridine, which may simultaneously be used as solvent, at temperatures of between −25° C. and 250° C., but preferably at temperature of between −10° C. and the boiling temperature of the solvent used. The reaction may also be carried out without a solvent and furthermore any water formed during the reaction may be removed by azeotropic distillation, e.g. by heating with toluene using a water separator, or by adding a drying agent such as magnesium sulphate or molecular sieve.

The compounds of general formula I have at least one chiral center and can, therefore, exist in the form of various stereoisomers. Te invention embraces all of these stereoisomers and mixtures thereof. Mixtures of these stereoisomers can be resolved by conventional methods, e.g. by column chromatography on a chiral phase, by fractional crystallization of the diastereomeric salts or by column chromatography of their conjugates with optically active auxiliary acids such as tartaric acid, O,O-dibenzoyl-tartaric acid, camphor acid, camphorsulfonic acid or α-methoxy-phenylacetic acid.

The compounds may also be converted into the acid addition salts thereof, particularly the pharmaceutically acceptable acid addition salts with inorganic or organic acids. Suitable acids for this include, for example, hydrochloric, hydrobromic, sulfuric, phosphoric, lactic, citric, tartaric, succinic, maleic or fumaric acid.

The compounds of general formulae II to IX used as starting materials are known from the literature in some cases or may be obtained using methods known from the literature.

Thus, for example, a compound of general formula II is obtained by halogenation of the corresponding cyclohexanone, which is in turn prepared by oxidation of the corresponding cyclohexanol and optional subsequent alkylation and/or acylation.

The compounds of general formulae VI, VII and VIII used as starting materials are obtained by condensation of a corresponding α-bromo-cyclohexanone with a corresponding thiourea.

As already mentioned hereinbefore, the compounds of general formula I wherein at least one of the groups $R_1$ to $R_4$ represents one of the acyl groups mentioned above are valuable intermediate products for preparing the compounds of general formula I wherein $R_1$ to $R_4$ have the meanings given to $R_1$ to $R_4$ hereinbefore, with the exception of the acyl groups referred to hereinbefore. These compounds and the pharmaceutically acceptable acid addition salts thereof have valuable pharmacological properties, particularly a hypotensive effect on blood pressure, a heart rate lowering effect and an effect on the central nervous system, particularly a stimulant effect on the dopamine receptors.

For example, therefore, in order to investigate the effect on presynaptic dopamine receptors, the following compounds A=2-amino-6-dimethylamino-4,5,6,7-tetrahydrobenzthiazol-dihydrochloride,
B=2-amino-6-pyrrolidino-4,5,6,7-tetrahydrobenzthiazol-dihydrochloride,
C=2-amino-6-n-propylamino-4,5,6,7-tetrahydrobenzthiazol-dihydrochloride,
D=2-allylamino-6-dimethylamino-4,5,6,7-tetrahydrobenzthiazol-dihydrochloride,
E=6-[N-ally-N-(4-chloro-benzyl)-amino]-2-amino-4,5,6,7-tetrahydro-benzthiazol-dihydrochloride and
F=2-amino-6-diallylamino-4,5,6,7-tetrahydrobenzthiazol-dihydrochloride were tested first for their effect on the exploratory activity of mice and then, after any effect on postsynaptic dopamine receptors had been clarified (motility in animals pretreated with reserpine), the effect on dopamine turnover and dopamine synthesis was determined, as follows:

1. Inhibition of the exploratory activity

The activity was measured in observation cages fitted with an infra-red light barrier. The frequency of interruption of the light beam by a group of 5 mice within 5 minutes. Groups of 5 animals are given the test substance, unless otherwise specified, in a dosage of 10 mg/kg by subcutaneous injection. One hour later the animals are moved into the observation cages where their exploratory activity over a period of 5 minutes is immediately measured. In parallel or alternately with groups treated with test substance, control groups treated with common salt are investigated (0.9% solution; 0.1 ml/10 g of body weight by subcutaneous route).

The results are assembled in the following table:

| Substance | Dosage (mg/kg s.c.) | Inhibition of activity in percent compared with controls treated with common salt |
|---|---|---|
| A | 2.7[1] | 50 |
| B | 10.0 | 94 |
| C | 10.0 | 20[2] |
| D | 10.0 | 76[2] |
| E | 10.0 | 56[2] |
| F | 10.0 | 60[2] |

[1] read off from the dosage/activity curve in the range from 1–10 mg/kg subcutaneously
[2] measurement of exploration: 75 minutes after administration of the substance 2. Determining the inhibition of dopamine turnover The inhibition of dopamine turnover was measured in mice. In animals treated with α-methylparatyrosine (AMPT) (250 mg/kg by intraperitoneal route) 15 minutes into the experiment, the dopamine concentration throughout the brain decreases as the test progresses. By administering substances which act on autoreceptors, the dopamine reduction (compared with control animals treated with common salt solution) can be prevented.

Test substances are administered at time O of the experiment in a dosage of 5 mg/kg s.c., unless otherwise stated. Four hours and 15 minutes into the experiment the animals are killed and the brains are subjected to dopamine determination using high pressure liquid chromatography with electrochemical detection. This determines the percentage inhibition, caused by the test substance, of the dopamine reduction induced by AMPT.

| Substance | Dosage (mg/kg s.c.) | % inhibition of AMPT effect |
|---|---|---|
| A | 0.95[1] | 50 |
| B | 5 | 67 |
| D | 5 | 52 |
| E | 5 | 32 |

[1] read off from the dosage/activity curve in the range from 0.5–3 mg/kg s.c.

3. Determining the inhibiton of dopamine synthesis

For this purpose, 5 animals are given the test substance in a dosage of 10 mg/kg s.c., unless otherwise stated. After 5 minutes, 750 mg/kg of γ-butyrolactone are administered by intraperitoneal route in order to rule out the effect of postsynaptic feed back loops on the rate of dopamine synthesis by blocking the presynaptic impulse line. This results in a considerable increase in the synthesis of DOPA or dopamine. In order to inhibit the decarboxylation of DOPA, 200 mg/kg of 3-hydroxybenzyl-hydrazinhydrochloride are administered by intraperitoneal route after a further 5 minutes. Forty minutes after administration of the substance the animals are killed and the corpus striatum is prepared. The DOPA content is measured by HPLC with electrochemical detection (standard: dihydroxybenzylamine).

The percentage inhibition, produced by the test substance, of the DOPA accumulation stimulated by γ-butyrolactone compared with the controlled animals treated with 0.9% common salt solution is determined.

The results of this experiment are shown in the following table:

| Substance | Dosage (mg/kg s.c.) | Inhibition of DOPA accumulation in percent compared with controls treated with common salt |
|---|---|---|
| A | 0.55[1] | 50 |

| Substance | Dosage (mg/kg s.c.) | Inhibition of DOPA accumulation in percent compared with controls treated with common salt |
|---|---|---|
| C | 10 | 60 |

[1] read off from the dosage/activity curve in the range from 0.1–1.0 mg/kg subcutaneous route.

4. Determining the anti-Parkinsonism activity or the activity against Parkinson's disease The discovery of the neurotoxin 1-methyl-4-phenyl-1,2,3,6-tetrahydropyridine (MPTP) (Langston et al., Science 219, 979 (1983)) provided an animal model for Parkinson's disease.

The irreversible neurological syndrome triggered by MPTP in man and in monkeys largely resembles the idiopathic Parkinson's disease in its clinical, pathological, biochemical and pharmacological characteristics (Markey et al., Nature 311, 464 (1984)). The reason for this convincing similarity is the fact that MPTP selectively destroys the small group of dopaminergic nerve cells in the substantia nigra of the brain which are also destroyed by degenerative processes in naturally occurring Parkinson's disease. There is even some speculation that the cause of idiopathic Parkinson's disease is MPTP or a similar compound forming in the organism (Synder, S.H., Nature 311, 514 (1984)). Possibly as a result of the specific metabolism of MPTP, the clinical impression of the MPTP-Parkinson picture has hitherto been demonstrated only in monkeys and man.

The MPTP model realised in Rhesus monkeys is therefore exceptionally suitable for testing the activity of anti-Parkinson's disease drugs. Seven Rhesus monkeys were given MPTP (for 3 days 1×0.15 mg/kg i.m. daily, 3 days' break, then 3 days 1×0.30–0.40 mg/kg daily) and showed the following symptoms; the animals were akinetic and not capable of taking water or food. They showed a typical bowed posture; occasionally, cataleptic states occured. The extremities showed a rigor which was interspersed by clonic convulsions on passive movement. As a rule, voluntary movements of the rump and the extremities could not be triggered even by very powerful and painful stimulation.

After intramuscular administration of compound C (10–100 μg/kg) voluntary movements first occured after a time interval of 5 to 10 minutes, which were followed in the subsequent 10 to 30 minutes by a gradual, extensive normalisation of the motor function. The animals were capable of taking food. They stayed perfectly upright and straight inside their cages and were also satisfactory in terms of their vigilance and species-specific behaviour. The only residual symptoms recorded were an occasional transient and slight resting tremor and a reduction in rough strength. There was no sedation. Circulation in the skin appeared to be greater than before the compound C was administered.

The effect of compound C diminished after about 5 to 7 hours and the animals reverted to the Parkinson symptoms described above; a fresh administration of this compound again leads to an improvement or substantial removal of the clinically pathological manifestations. The advantageous effects of the compounds were thus reproduced several times in each individual animal.

No side effects were detected at the dosages used hitherto.

Moreover, the compounds prepared according to the invention are largely non-toxic. Thus, when the substances were tested in mice at dosages of between 27 and 50 mg/kg s.c., no deaths were recorded.

In view of their pharmacological properties, the compounds of general formula I prepared according to the invention and the pharmaceutically acceptable acid addition salts thereof are suitable for the treatment of central nervous, neuropsychiatric diseases, particularly schizophrenia, for the treatment of Parkinsonism or Parkinson's disease and/or for treating circulatory disorders, particularly hypertension.

For pharmaceutical use, the new compounds and the pharmaceutically acceptable acid addition salts thereof, optionally combined with other active substances, may be incorporated in the conventional galenic preparations such as plain or coated tablets, powders, suppositories, suspensions, drops or ampoules. The individual dose is from 0.01 to 0.5 mg/kg of body weight, preferably 0.1 to 0.3 mg/kg of body weight, 1 to 4 times a day.

The examples which follow are intended to illustrate the invention:

EXAMPLE A

4-[N-(4-Chloro-benzyl)-amino]-cyclohexanol 75.8 g (0.5 Mol) of 4-amino-cyclohexanolhydrochloride are dissolved in 60 ml of water and, after the addition of 36 g (0.26 Mol) of potassium carbonate and 500 ml of toluene, boiled with a water separator until the separation of water has ended. Then 71.7 g (0.5 Mol) of 4-chlorobenzaldehyde are slowly added with further boiling using the water separator. After the calculated quantity of water has been separated, the residue is added to water and the toluene phase is separated off and concentrated. The concentration residue is dissolved in 500 ml of ethanol and 19 g (0.5 Mol) of sodium borohydride are added in batches with stirring. After standing overnight, the mixture is concentrated, mixed with water and extracted with chloroform. After drying and concentrating the extracts, the residue is recrystallised from ethyl acetate.

Yield: 93.4 g (78% of theory), M.p.: 103°–104° C. Calculated: C, 65.12; H, 7.57; N, 5.84; Cl, 14.79. Found: C, 65.21; H, 7.68; N, 5.93; Cl, 14.65.

The following compound was prepared analogously to Example A using propionaldehyde: 4-n-propylamino-cyclohexanol Yield: 12.4% of theory, M.p.: 20° C. Calculated: m/e=157. Found: m/e=157.

EXAMPLE B

4-[N-(4-Chloro-benzyl)-methylamino]-cyclohexanol 7.2 g (30 mMol) of 4-[N-(4-chloro-benzyl)-amino]-cyclohexanol are dissolved in 30 ml of dimethyl-formamide, and after the addition of 2.2 g (16 mMol) of potassium carbonate, 4.26 g (30 mMol) of methyliodide are added dropwise. When the slightly exothermic reaction has ended, the mixture is concentrated by evaporation, mixed with water and extracted with chloroform. The concentrated extracts are chromatographed on silica gel to purify them (eluant; methylene chloride/methanol=20/1).

Yield: 3.3 g (43.4% of theory). M.p.: 74°–75° C. Calculated: C, 66.26; H, 7.94; N, 5.52; Cl, 13.97. Found: C, 66.36; H, 7.95; N, 5.46; Cl, 13.81.

The following compounds were prepared analogously to Example B:

4-Hexamethyleneimino-cyclohexanol

Prepared from 4-amino-cyclohexanol and 1,6-dibromohexane.

Yield: 47.3% of theory, M.p.: <20° C. Calculated: m/e=197. Found: m/e=197.

4-Diallylamino-cyclohexanol

Prepared from 4-amino-cyclohexanol and allylbromide.

Yield: 51% of theory, M.p.: <20° C. Calculated: m/e=195. Found: m/e=195.

4-Piperidino-cyclohexanol

Prepared from 4-amino-cyclohexanol and 1,5-dibromopentane.

Yield: 65.8% of theory, M.p.: <20° C. Calculated: m/e=183. Found: m/e=183.

4-Pyrrolidino-cyclohexanol

Prepared from 4-amino-cyclohexanol and 1,4-dibromo-butane.

Yield: 35.8% of theory, M.p.: <20° C. Calculated: m/e=169. Found: m/e=169.

EXAMPLE C

4-Diethylamino-cyclohexanol 28.75 g (0.25 Mol) of 4-amino-cyclohexanol are dissolved in 150 ml of water, with the addition of 20 g (0.5 Mol) of sodium hydroxide and then 65.6 ml (0.5 Mol) of diethylsulfate are added dropwise. The mixture then heats up to 65° C. It is stirred for an hour at 70° C., then poured onto ice and extracted with chloroform.

Yield: 18.2 g (42.5% of theory, M.p.: <20° C. Calculated: m/e=171. Found: m/e=171.

EXAMPLE D

4-[N-(4-Chloro-benzyl)-amino]-cyclohexanone 23.9 g (0.1 Mol) of 4-[N-(4-chlorobenzyl)-amino]-cyclohexanol are suspended in 125 ml of ice water and 32 ml of concentrated sulphuric acid are added. Then 29.4 g (0.1 Mol) of potassium dichromate are added in 2 batches and the mixture is heated for 5 hours at 50° C. It is then cooled, made alkaline with sodium hydroxide solution and extracted with chloroform. After concentration, a yellowish oily liquid is obtained.

Yield: 8.2 g (34% of theory, M.p.: <20° C. Calculated: m/e=237/239. Found: m/e=237/239.

The following compounds were prepared analogously to Example D:

4-[N-(4-Chloro-benzyl)-methylamino]-cyclohexanone

Yield: 38% of theory, M.p.: <20° C. Calculated: m/e=251/253. Found: m/e=251/253.

4-Diallylamino-cyclohexanone

Yield: 21% of theory, M.p.: <20° C. Calculated: m/e=193. Found: m/e=193.

4-Piperidino-cyclohexanone

Yield: 22.2% of theory, M.p.: <20° C. Calculated: m/e=181. Found: m/e=181.

4-Pyrrolidino-cyclohexanone

Yield: 45.1% of theory, M.p.: <20° C. Calculated: m/e=167. Found: m/e=167.

4-Diethylamino-cyclohexanone

Yield: 49.7% of theory, M.p.: <20° C. Calculated: m/e=169. Found: m/e=169.

4-n-Propylamino-cyclohexanone

Yield: 33% of theory, M.p.: <20° C. Calculated: m/e=155. Found: m/e=155.

EXAMPLE E

4-[N-(4-Chloro-benzyl)-methylamino]-cyclohexanone 8.4 g (35 mMol) of 4-[N-(4-chloro-benzyl)-amino]-cyclohexanone are dissolved in 50 ml of absolute dimethylformamide and, after the addition of 2.6 g (18.7 mMol) of potassium carbonate, 5.0 g (35 mMol) of methyliodide are added dropwise at 25°-30° C. After standing overnight the mixture is concentrated, mixed with water and extracted with chloroform. The extracts are dried and concentrated.

Yield: 8.1 g (93% of theory, M.p.: <20° C. Calculated: m/e=251/253. Found: m/e=251/253.

The following compounds were prepared analogously to Example E:

4-[N-Allyl-N-(4-chloro-benzyl)-amino]-cyclohexanone

Yield: 70.7% of theory, M.p.: <20° C. Calculated: m/e=277/279. Found: m/e=277/279.

4-[N-(4-Chloro-benzyl)-ethylamino]-cyclohexanone

Yield: 30% of theory, M.p.: <20° C. Calculated: m/e=265/267. Found: m/e=265/267.

EXAMPLE F

4-Hexamethyleneimino-cyclohexanone

At 20° to 25° C. a solution of 47 g (0.5 Mol) of 4-hexamethyleneimino-cyclohhexanol in 300 ml of methylenechloride is added dropwise to a suspension of 107.5 g (0.5 Mol) of pyridiniumchlorochromate and 40 g (0.5 Mol) of sodium acetate in 700 ml of methylenechloride. After stirring for one hour at 20° C. the mixture is poured onto ice water and sodium hydroxide solution and extracted with methylene chloride. After drying and concentration of the extracts a coloured oily liquid is left.

Yield: 16.8 g (35.8% of theory), M.p.: <20° C. Calculated: m/e=195. Found: m/e=195.

EXAMPLE 1

2-Amino-6-dimethylamino-4,5,6,7-tetrahydro-benzthiazole-dihydrochloride 2.82 g (0.02 Mol of 4-dimethylamino-cyclohexanone are dissolved in 20 ml of glacial acetic acid, mixed with 4.7 ml of 36% of hydrobromic acid in glacial acetic acid and then a solution of 1.0 ml (0.02 Mol) of bromine in 12 ml of glacial acetic acid is added dropwise with cooling. The mixture is then concentrated by evaporation in vacuo and the residue is triturated several times with diethylether. The ether extracts are discarded and the residue is dissolved in 50 ml of ethanol. After 3.04 g (40 mMol) of thiourea have been added the mixture is refluxed for 5 hours. It is then concentrated by evaporation, made alkaline with sodium hydroxide solution and extracted with chloroform. After drying and concentration of the extracts, the residue is purified by column chromatography on silica gel (eluant: chloroform/methanol =1/1). Then the base (mp: 191° C.) is dissolved in acetone and converted into the dihydrochloride with isopropanolic hydrochloric acid.

Yield: 1.09 g (20% of theory), M.p.: 272° C. Calculated: C, 40.00; H, 6.34; N, 15.55; Cl, 26.24. Found: C, 39.63; H, 6.55; N, 15.31; Cl, 26.29.

The following tetrahydrobenzthiazoles were prepared analogously to Example 1 from the corresponding ketones:

2-Amino-6-diethylamino-4,5,6,7-tetrahydro-benzthiazole

Yield: 25% of theory.
M.p.: 182°–183° C.
Calculated: C, 58.62; H, 8.49; N, 18.64. Found: C, 58.65; H, 8.72; N, 18.50.

2-Amino-6-piperidino-4,5,6,7-tetrahydro-benzthiazole-dihydrochloride

Yield: 13% of theory.
M.p.: 280° C.
Calculated: C, 46.45; H, 6.82; N, 13.55; Cl, 22.85. Found: C, 46.37; H, 6.75; N, 13.41; Cl, 22.95.

2-Amino-6-pyrrolidino-4,5,6,7-tetrahydro-benzthiazole

Yield: 24.4% of theory.
M.p.: 204°–206° C.
Calculated: C, 59.15; H, 7.67; N, 18.81. Found: C, 59.50; H, 7.74; N, 18.95.

2-Amino-6-diallylamino-4,5,6,7-tetrahydro-benzthiazole-dihydrochloride

Yield: 19% of theory.
M.p.: 242° C.
Calculated: C, 48.44; H, 6.56; N, 13.03; Cl, 22.00. Found: C, 47.90; H, 6.49; N, 12.95; Cl, 22.21.

2-Amino-6-[N-(4-chloro-benzyl)-amino]-4,5,6,7-tetrahydro-benzthiazole

Yield: 35% of theory.
M.p.: 146° C.
Calculated: C, 57.23; H, 5.49; N, 14.30; Cl, 12.06. Found: C, 56.93; H, 5.56; N, 13.86; Cl, 12.04.

2-Amino-6-[N-(4-chloro-benzyl)-methylamino]-4,5,6,7-tetrahydro-benzthiazole

Yield: 36% of theory.
M.p.: 163° C.
Calculated: C, 58.69; H, 5.89; N, 13.64; Cl, 11.51. Found: C, 58.50; H, 5.94; N, 13.49; Cl, 11.55.

2-Amino-6-[N-(4-chloro-benzyl)-ethylamino]-4,5,6,7-tetrahydro-benzthiazole-dihydrochloride Yield: 49% of theory.
M.p.: 258° C. (decomposition).
Calculated: C, 48.67; H, 5.61; N, 10.64; Cl, 26.94. Found: C, 48.30; H, 5.85; N, 10.57; Cl, 26.97.

2-Amino-6-[N-allyl-N-(4-chloro-benzyl)-amino]-4,5,6,7-tetrahydro-benzthiazole-dihydrochloride Yield: 46.5% of theory.
M.p.: 240° C. (decomposition)
Calculated: C, 50.19; H, 5.45; N, 10.33; Cl, 26.14. Found: C, 49.84; H, 5.68; N, 9.97; Cl, 26.04.

2-Amino-6-hexamethyleneimino-4,5,6,7-tetrahydro-benzthiazole-dihydrochloride

Yield: 15.4% of theory.
M.p.: 295° C. (decomposition).
Calculated: C, 48.17; H, 7.14; N, 12.95; Cl, 21.86. Found: C, 47.90; H, 7.34; N, 12.44; Cl, 21.64.

2-Allylamino-6-dimethylamino-4,5,6,7-tetrahydro-benzthiazole-dihydrochloride

Prepared from 4-dimethylamino-cyclohexanone by bromination and subsequent reaction with allylthiourea.
Yield: 64% of theory.
M.p.: 248° C.,
Calculated: C, 46.45; H, 6.82; N, 13.54; Cl, 22.85. Found: C, 46.30; H, 7.00; N, 13.29; Cl, 22.99.

2-Amino-5-dimethylamino-4,5,6,7-tetrahydro-benzthiazole-dihydrochloride

Prepared from 3-dimethylamino-cyclohexanone.
Yield: 33% of theory.
M.p.: 194° C.
Calculated: C, 40.00; H, 6.34; N, 15.55; Cl, 26.24. Found: C, 39.74; H, 6.37; N, 15.15; Cl, 25.96.

2-Amino-5-morpholino-4,5,6,7-tetrahydro-benzthiazole-dihydrochloride

Prepared from 3-morpholino-cyclohexanone.
Yield: 7.4 g (20% of theory).
M.p.: 237°–238° C.
Calculated: C, 42.31; H, 6.13; N, 13.46. Found: C, 42.00; H, 6.29; N, 13.13.

EXAMPLE 2

2,6-Diamino-4,5,6,7-tetrahydro-benzthiazole-dihydrochloride (a) 4-(Phthalimido)-cyclohexanol 75.5 g (0.5 Mol) of 4-aminocyclohexanolhydrochloride and 74.0 g (0.5 Mol) of phthalic acid anhydride are mixed with 65 g (0.5 Mol) of ethyldiisopropyl-amine and 1000 ml of toluene and boiled for 36 hours with a water separator. Then water is added, the toluene phase is separated off and the aqueous phase is extracted several times with chloroform. The organic phases are combined, dried and concentrated. The concentration residue is recrystallised from isopropanol.

Yield: 95 g (77.8% of theory).
M.p.: 175°–176° C.

(b) 4-(Phthalimido)-cyclohexanone 95 g (0.388 Mol) of 4-(phthalimido)-cyclohexanol are dissolved in 600 ml of chloroform and, after the addition of 450 ml of water and 120 ml of sulfuric acid, 90 g (0.3 Mol) of potassium dichromate are added in batches. The internal temperature of the mixture is maintained at between 25° and 30° C. by slight cooling. The mixture is stirred for a further 3 hours, then the chloroform phase is separated off and the mixture extracted twice more with chloroform. After drying and concentration of the extracts 82 g (86.9% of theory) are obtained.

(c) 2-Amino-6-phthalimido-4,5,6,7-tetrahydro-benzthiazol 48.6 g (0.2 Mol) of 4-(phthalimido)cyclohexanone are brominated analogously to Example 1 with 32 g (0.2 Mol) of bromine and then converted with thiourea into the 2-amino-6-phthalimido-4,5,6,7-tetrahydro-benzthiazol.

Yield: 30 g (50% of theory).
M.p.: 244°–246° C. (decomposition).
Calculated: C, 60.18; H, 4.38; N, 14.04. Found: C, 60.05; H, 4.25; N, 13.95.

(d) 2,6-Diamino-4,5,6,7-tetrahydro-benzthiazole-dihydrochloride 9.5 g (31.7 mMol) of 2-amino-6-phthalmido-4,5,6,7-tetrahydro-benzthiazole are suspended in 100 ml of ethanol and, after the addition of 1.8 g (36 mMol) of hydrazine hydrate, refluxed for 2 hours. The mixture is then concentrated and purified by column chromatography on silica gel using methanol as eluant. Then the dihydrochloride is precipitated in ethanol with ethanolic hydrochloric acid.

Yield: 2.0 g (26% of theory).
M.p.: >315° C. (decomposition).
Calculated: C, 34.72; H, 5.41; N, 17.35; Cl, 29.25. Found: C, 35.00; H, 5.26; N, 16.95; Cl, 29.10.

EXAMPLE 3

6-Acetylamino-2-amino-4,5,6,7-tetrahydro-benzthiazole-hydrobromide 160 g (1.0 Mol) of bromine are added dropwise to a solution of 155 g (1.0 Mol) of 4-acetylamino-cyclohexanone in 1.5 l of glacial acetic acid. The mixture is stirred for 3 hours at ambient temperature. 152.0 g (2.0 Mol) of thiourea are added to the reaction mixture and the resulting mixture is refluxed for 30 minutes. After cooling, the crystals precipitated are suction filtered and washed with water and acetone.

Yield: 73 g (37% of theory).
M.p.: 292°-293° C. (decomposition).
Calculated: C, 36.99; H, 4.83; N, 14.38. Found: C, 36.82; H, 4.76; N, 14.18.

By stirring the hydrobromide in aqueous potassium carbonate solution and subsequently suction filtering, the free base is obtained, m.p. 194°-196° C. (methanol).

The following compounds were prepared analogously to Example 3:

6-Acetylamino-2-allylamino-4,5,6,7-tetrahydro-benzthiazole

Yield: 46% of theory.
M.p.: 194°-196° C.
Calculated: m/e=251. Found: m/e=251.

6-Acetylamino-2-methylamino-4,5,6,7-tetrahydro-benzthiazole

Yield: 64% of theory.
M.p.: 238°-240° C.
Calculated: C, 53.30; H, 6.71; N, 18.65. Found: C, 53.18; H, 6.78; N, 18.41.

6-Acetylamino-2-dimethylamino-4,5,6,7-tetrahydro-benzthiazole

Yield: 51% of theory.
M.p.: 170°-171° C.
Calculated: C, 55.20; H, 7.16; N, 17.56. Found: C, 55.15; H, 7.17; N, 17.58.

EXAMPLE 4

2,6-Diamino-4,5,6,7-tetrahydro-benzthiazole-dihydrobromide 3 g (0.01 Mol) of 6-acetylamino-2-amino-4,5,6,7-tetrahydro-benzthiazole-hydrobromide are dissolved in 20 ml of semi-concentrated hydrobromic acid and refluxed for 6 hours. The solution is then concentrated by evaporation and the residue recrystallised from methanol.

Yield: 2.8 g (82% of theory).
M.p.: >315° C., Melting point of the base: 233°-236° C.
Calculated: C, 25.39; H, 3.96; N, 12.69. Found: C, 25.34; H, 3.93; N, 12.51.

The following compounds were prepared analogously to Example 4:

6-Amino-2-methylamino-4,5,6,7-tetrahydro-benzthiazole-hydrobromide

Yield: 57% of theory.
M.p.: 262°-263° C.
Calculated: C, 36.37; H, 5.34; N, 15.90. Found: C, 36.30; H, 5.45; N, 15.82.

2-Allylamino-6-amino-4,5,6,7-tetrahydro-benzthiazole-oxalate

Yield: 52% of theory.
M.p.: 164°-165° C. (decomp.).
Calculated: m/e=209. Found: m/e=209.

6-Amino-2-dimethylamino-4,5,6,7-tetrahydro-benzthiazole-dihydrobromide

Yield: 45% of theory.
M.p.: >270° C. (decomp.).
Calculated: C, 30.10; H, 4.77; N, 11.70. Found: C, 30.13; H, 4.84; N, 11.68;

EXAMPLE 5

2-Amino-6-[N-(2-phenyl-ethyl)-amino]-4,5,6,7-tetrahydro-benzthiazole-dihydrochloride To a solution of 3.4 g (0.02 Mol) of 2,6-diamino-tetrahydro-benzthiazole in 34 ml of dimethylformamide are added 5 g (0.022 Mol) of 2-phenyl-ethylbromide and 2.6 g of potassium carbonate and the reaction mixture is stirred at 100° C. for 3 hours. The potassium bromide precipitated is then suctioned off and the solvent is distilled off. The residue is chromatographed on silica gel (ethyl acetate/methanol=80/20+3% ammonia. The desired compound crystallises out from ethereal hydrochloric acid.

Yield: 2.1 g (30% of theory).
M.p.: 289°-291° C.
Calculated: C, 52.02; H, 6.11; N, 12.13. Found: C, 51.82; H, 6.13; N, 12.16

The following compounds were prepared analgously to Example 5:

2-Amino-6-isopropylamino-4,5,6,7-tetrahydro-benzthiazole-dihydrochloride

Yield: 28% of theory.
M.p.: 295°-296° C. (decomp.).
Calculated: C, 42.25; H, 6.74; N, 14.78. Found: C, 41.95; H, 7.09; N, 14.50.

2-Amino-6-isobutylamino-4,5,6,7-tetrahydro-benzthiazole-dihydrochloride

Yield: 35% of theory.
M.p.: 268° C. (decomp.).
Calculated: C, 44.29; H, 7.10; N, 14.09. Found: C, 43.97; H, 7.17; N, 13.97.

6-Allylamino-2-amino-4,5,6,7-tetrahydro-benzthiazole-dihydrochloride

Yield: 38% of theory.
M.p.: 282°-283° C. (decomp.).
Calculated: C, 42.56; H, 6.07; N, 14.89. Found: C, 42.17; H, 6.07; N, 14.71.

2-Amino-6-[N-(2-chloro-benzyl)-amino]-4,5,6,7-tetrahydro-benzthiazole-dihydrochloride Yield: 40% of theory.

M.p.: >280° C. (decomp.).
Calculated: C, 45.85; H, 4.95; N, 11.45. Found: C, 45.50; H, 4.86; N, 11.08.

2-Amino-6-propargylamino-4,5,6,7-tetrahydro-benzthiazole-dihydrochloride

Yield: 35% of theory.
M.p.: 268°-270° C. (decomp.).
Calculated: C, 42.86; H, 5.40; N, 15.00. Found: C, 42.78; H, 5.59; N, 14.79.

2-Amino-6-methylamino-4,5,6,7-tetrahydro-benzthiazole-dihydrobromide

Yield: 25% of theory.
M.p.: 312°-313° C. (decomp.).
Calculated: C, 27.84; H, 4.38; N, 12.18. Found: C, 27.78; H, 4.46; N, 12.21.

EXAMPLE 6

2-Amino-6-di-n-propylamino-4,5,6,7-tetrahydro-benzthiazole-dihydrochloride-monohydrate To a solution of 3.4 g (0.02 Mol) of 2,6-diamino-4,5,6,7-tetrahydro-benzthiazole in 50 ml of methanol are added 10 g (0.08 Mol) of n-propylbromide and 11.1 g of potassium carbonate and the mixture is refluxed for 3 days. Then 100 ml of water are added and the mixture is extracted with ethylacetate. The solvent is distilled off and the residue is chromatographed on silica gel (eluant: methylenechloride/methanol=80/20). The corresponding fraction is concentrated by evaporation and the desired compound is precipitated in the form of the hydrochloride.

Yield: 1.9 g (28% of theory).
M.p.: 271°-273° C.
Calculated: C, 45.34; H, 7.90; N, 12.20. Found: C, 45.00; H, 7.98; N, 12.00.

EXAMPLE 7

2-Amino-6-n-butylamino-4,5,6,7-tetrahydro-benzthiazole-dihydrochloride

To a solution of 3.4 g (0.02 Mol) of 2,6-diamino-4,5,6,7-tetrahydro-benzthiazole in 34 ml of dimethylformamide are added 1.8 g (0.022 Mol) of n-butanal and the mixture is heated to 50° C. for 1 hour. After cooling, the reaction solution is mixed with 0.8 g (0.02 Mol) of sodium borohydride and heated to 50° C. for 30 minutes. The solvent is largely eliminated in vacuo. Whilst cooling with ice, the residue is mixed with 20 ml of water and 2N hydrochloric acid until a pH of 1 is obtained. The aqueous solution is extracted with ethylacetate and the organic phase discarded. The aqueous phase is mixed with potassium carbonate until an alkaline reaction is obtained and then extracted with ethyl acetate. The organic phase is dried and concentrated. The compound crystallizes out when ethereal hydrochloric acid is added.

Yield: 2.3 g (39% of theory).
M.p.: 254°-256° C.
Calculated: C, 44.29; H, 7.10; N, 14.09. Found: C, 44.44; H, 7.31; N, 14.07.

The following compounds were prepared analogously to Example 7:

2-Amino-6-ethylamino-4,5,6,7-tetrahydro-benzthiazole-dihydrochloride

Yield: 38% of theory.
M.p.: 296°-297° C.
Calculated: C, 40.00; H, 6.34; N, 15.55. Found: C, 39.97; H, 6.41; N, 15.35.

2-Amino-6-n-pentylamino-4,5,6,7-tetrahydro-benzthiazole-semifumarate

Yield: 42% of theory.
M.p.: >270° C.
Calculated: C, 56.54; H, 7.79; N, 14.13. Found: C, 56.13; H, 7.80; N, 13.97.

2-Amino-6-n-hexylamino-4,5,6,7-tetrahydro-benzthiazole-dihydrochloride

Yield: 49% of theory.
M.p.: 272°-274° C.
Calculated: C, 47.85; H, 7.72; N, 12.88. Found: C, 47.96; H, 7.65; N, 12.71.

2-Amino-6-n-propylamino-4,5,6,7-tetrahydro-benzthiazole-dihydrochloride

Yield: 42% of theory.
M.p.: 286°-288° C.
Calculated: C, 42.25; H, 6.74; N, 14.78. Found: C, 42.05; H, 6.77; N, 14.57.

(−)2-Amino-6-n-propylamino-4,5,6,7-tetrahydro-benzthiazole-dihydrochloride

M.p.: 270°-272° C.
$\alpha_D^{20} = -56°$ (c=1, methanol), (+)2-Amino-6-n-propylamino-4,5,6,7-tetrahydro-benzthiazole-dihydrochloride M.p.: 270°-272° C.
$\alpha_D^{20} = +56°$ (c=1, methanol), 2-Amino-6-cyclopentylamino-4,5,6,7-tetrahydro-benzthiazole-dioxalate Yield: 36% of theory.
M.p.: 212°-213° C.,
Calculated: C, 46.04; H, 5.55; N, 10.07. Found: C, 45.95; H, 5.28; N, 10.08.

2-Amino-6-cyclohexylamino-4,5,6,7-tetrahydro-benzthiazole-dihydrochloride

Yield: 38% of theory.
M.p.: 288°-290° C.
Calculated: C, 48.14; H, 7.15; N, 12.96. Found: C, 47.88; H, 7.16; N, 12.74.

EXAMPLE 8

6-Ethylamino-2-methylamino-4,5,6,7-tetrahydro-benzthiazole-dihydrochloride

A solution of 1 g (0.0044 Mol) of 6-acetylamino-2-methylamino-4,5,6,7-tetrahydro-benzthiazole in 20 ml of absolute tetrahydrofuran is mixed with 0.4 g (0.01 Mol) of lithiumaluminium hydride and refluxed for 2 hours. After cooling, 50 g of a 40% diammonium tartrate solution are added dropwise. The organic phase is separated off and concentrated by evaporation. The residue is chromatographed on silica gel (eluant: methylene chloride/methanol=80/20). The corresponding fraction is concentrated by evaporation. The compound crystallizes out when ethereal hydrochloric acid is added.

Yield: 0.3 g (33% of theory).
M.p.: 260° C.,
Calculated: m/e=211. Found: m/e=211.

The following compounds were prepared analogously to Example 8:

2-Allylamino-6-ethylamino-4,5,6,7-tetrahydro-benzthiazole-dihydrochloride

Yield: 37% of theory.
M.p.: 218°-220° C. (decomp.).
Calculated: C, 46.45; H, 6.82; N, 13.54. Found: C, 46.60; H, 7.03; N, 13.66.

2-Dimethylamino-6-ethylamino-4,5,6,7-tetrahydro-benzthiazole-oxalate hydrate

Yield: 20% of theory.
M.p.: 189°-190° C.
Calculated: C, 46.83; H, 6.95; N, 12.60. Found: C, 47.03; H, 6.89; N, 12.49.

EXAMPLE 9

6-Acetylamino-2-benzoylamino-4,5,6,7-tetrahydro-benzthiazole

To a solution of 4.2 g (0.02 Mol) of 6-acetylamino-2-amino-4,5,6,7-tetrahydro-benzthiazole in 100 ml of absolute tetrahydrofuran are added 2.2 g (0.022 Mol) of triethylamine and 3.1 g (0.022 Mol) of benzoylchloride and the mixture is refluxed for 3 hours. The reaction mixture is mixed with water and extracted with ethyl acetate. The organic phase is concentrated by evaporation. The residue is recrystallized from methanol.
Yield: 3 g (48% of theory).
M.p.: >260° C.
Calculated: m/e=315. Found: m/e=315.

The following compounds were prepared analogously to Example 9:

2,6-Diacetylamino-4,5,6,7-tetrahydro-benzthiazole

Yield: 50% of theory.
M.p.: 258°-259° C.,
Calculated: m/e=252. Found: m/e=252.

6-Acetylamino-2-propionylamino-4,5,6,7-tetrahydro-benzthiazole

Yield: 44% of theory.
M.p.: >260° C.
Calculated: m/e=266. Found: m/e=266.

6-Acetylamino-2-phenylacetylamino-4,5,6,7-tetrahydro-benzthiazole

Yield: 78% of theory.
M.p.: 112° C.
Calculated: m/e=329. Found: m/e=329.

EXAMPLE 10

2-Benzylamino-6-ethylamino-4,5,6,7-tetrahydro-benzthiazole-dihydrochloride

To a solution of 1.2 g (3.2 mMol) of 6-acetylamino-2-benzoylamino-4,5,6,7-tetrahydro-benzthiazole in 50 ml of absolute tetrahydrofuran are added 0.24 g (64 mMol) of lithiumaluminiumhydride and the mixture is refluxed for 1 hour. It is then worked up as in Example 8.
Yield: 0.4 g (34% of theory).
M.p.: 242°-245° C.
Calculated: C, 53.33; H, 6.43; N, 19.68. Found: C, 53.59; H, 6.37; N, 19.42.

The following compounds were prepared analogously to Example 10:

2,6-Diethylamino-4,5,6,7-tetrahydro-benzthiazole-dihydrochloride

Yield: 38% of theory.
M.p.: 241°-243° C.,
Calculated: C, 44.29; H, 7.10; N, 14.09. Found: C, 44.06; H, 7.27; N, 13.85.

6-Ethylamino-2-n-propylamino-4,5,6,7-tetrahydro-benzthiazole-dihydrochloride

Yield: 32% of theory.
M.p.: 267°-268° C.,
Calculated: C, 46.15; H, 7.42; N, 13.46. Found: C, 45.95; H, 7.53; N, 13.33.

6-Ethylamino-2-[N-(2-phenyl-ethyl)-amino]-4,5,6,7-tetrahydro-benzthiazole-dihydrochloride-hemihydrate Yield: 26% of theory.
M.p.: 248°-251° C.
Calculated: C, 53.25; H, 6.84; N, 10.96. Found: C, 53.31; H, 6.64; N, 10.89.

2-(4-Chloro-benzylamino)-6-ethylamino-4,5,6,7-tetrahydro-benzthiazole-dihydrochloride Yield: 65% of theory.
M.p.: >260° C.
Calculated: C, 48.67; H, 5.62; N, 10.64. Found: C, 48.79; H, 5.80; N, 10.60.

2-(2-Chloro-benzylamino)-6-ethylamino-4,5,6,7-tetrahydro-benzthiazole-dihydrochloride.

Yield: 36% of theory.
M.p.: 251°-253° C.
Calculated: C, 48.67; H, 5.62; N, 10.64. Found: C, 48.57; H, 5.78; N, 10.57.

2-(3,4-Dichloro-benzylamino)-6-ethylamino-4,5,6,7-tetrahydro-benzthiazole-dihydrochloride Yield: 62.5% of theory.
M.p.: >260° C.,
Calculated: C, 44.77; H, 4.93; N, 9.79. Found: C, 44.85; H, 4.82; N, 9.96.

6-Acetylamino-2-ethylamino-4,5,6,7-tetrahydro-benzthiazole

Prepared from 2,6-diacetylamino-4,5,6,7-tetrahydro-benzthiazole at ambient temperature.
Yield: 33% of theory.
M.p.: 234°-235° C.
Calculated: m/e=238. Found: m/e=238.

6-Acetylamino-2-benzylamino-4,5,6,7-tetrahydro-benzthiazole prepared from 6-acetylamino-2-benzoylamino-4,5,6,7-tetrahydro-benzthiazole at ambient temperature.

6-Acetylamino-2-n-propylamino-4,5,6,7-tetrahydro-benzthiazole prepared from 6-acetylamino-2-propionylamino-4,5,6,7-tetrahydro-benzthiazole at ambient temperature.

6-Acetylamino-2-[N-(2-phenyl-ethyl)-amino]-4,5,6,7-tetrahydrobenzthiazole.

EXAMPLE 11

6-Amino-2-ethylamino-4,5,6,7-tetrahydro-benzthiazole-dihydrochloride

Prepared from 6-acetylamino-2-ethylamino,4,5,6,7-tetrahydro-benzthiazole analogously to Example 4.
Yield: 45% of theory.

M.p.: 155°–158° C.

Calculated: C, 40.00; H, 6.34; N, 15.55. Found: C, 39.86; H, 6.31; N, 15.26.

The following compounds were prepared analogously to Example 11:

6-Amino-2-benzylamino-4,5,6,7-tetrahydro-benzthiazole-dihydrobromide

6-Amino-2-n-propylamino-4,5,6,7-tetrahydro-benzthiazole-dihydrobromide

6-Amino-2-[N-(2-phenyl-ethyl)amino]-4,5,6,7-tetrahydro-benzthiazole-dihydrobromide.

EXAMPLE 12

2-Benzoylamino-6-dimethylamino-4,5,6,7-tetrahydro-benzthiazole-dihydrochloride 3.0 g (15 mMol) of 2-amino-6-dimethylamino-4,5,6,7-tetrahydro-benzthiazole are dissolved in 15 ml of pyridine and 2.1 g (15 mMol) of benzoylchloride are added dropwise. After standing overnight the mixture is concentrated, mixed with soda solution and extracted with chloroform. The chloroform extract is concentrated and then chromatographed on silica gel (eluant: methylenechloride/methanol=9/1). The isolated base (melting point 174° C.) is dissolved in acetone and the dihydrochloride is precipitated with isopropanolic hydrochloric acid.

Yield: 2.8 g (49% of theory).

M.p.: 284° C. (decomp.).

Calculated: C, 51.33; H, 5.65; N, 11.23; Cl, 18.94. Found: C, 51.51; H, 5.76; N, 11.32; Cl, 18.75.

EXAMPLE 13

6-Acetylamino-2-amino-4,5,6,7-tetrohydro-benzthiazole 3.1 g (20 mMol) of 4-acetylamino-cyclohexanone and 6.2 g (20 mMol) of formamidine-disulfidedihydrobromide are intimately mixed and heated in a heating bath at a temperature of 120°–130° C. for 2 hours with stirring. The mixture is then taken up in water, made alkaline with ammonia and extracted with chloroform. After the extracts have been dried they are concentrated by evaporation, triturated with acetone and suction filtered.

Yield: 1.8 g (42.6% of theory).

M.p.: 195° C.

Calculated: C, 51.17; H, 6.20; N, 19.89. Found: C, 51.09; H, 6.22; N, 19.75.

Starting from 4-dimethylamino-cyclohexanone the following compound was prepared analogously to Example 13:

2-Amino-6-dimethylamino-4,5,6,7-tetrahydro-benzthiazole

Yield: 21% of theory.

M.p.: 189°–190° C.

Calculated: C, 54.80; H, 7.66; N, 21.29. Found: C, 54.71; H, 7.53; N, 21.12.

EXAMPLE I

Tablet core containing 5 mg of 2-amino-6-dimethylamino-4,5,6,7-tetrahydro-benzthiazole-dihydrochloride

| Composition: 1 tablet core contains: | |
|---|---|
| Active substance | 5.0 mg |
| Lactose | 33.5 mg |
| Corn starch | 10.0 mg |
| Gelatine | 1.0 mg |
| Magnesium stearate | 0.5 mg |
| | 50.0 mg |

Preparation

A mixture of the active substance with lactose and corn starch is granulated with a 10% aqueous gelatine solution through a screen with a mesh size of 1 mm, dried at 40° C. and again rubbed through this screen. The granulate thus obtained is mixed with magnesium stearate and compressed to form tablet cores. The tablets must be prepared in darkened rooms.

Weight of core: 50 mg.

Punch: 4 mm, convex.

The tablet cores thus obtained are coated by the usual method with a coating consisting essentially of sugar and talc. The finished coated tablets are polished with bees wax.

Weight of coated tablet: 100 mg.

EXAMPLE II

Drops containing 5 mg of 2-amino-6-dimethylamino-4,5,6,7-tetrahydro-benzthiazole-dihydrochloride

| Composition: 100 ml of drops substance: | |
|---|---|
| Methylester-p-hydroxybenzoate | 0.035 g |
| n-Propylester-p-hydroxybenzoate | 0.015 g |
| Anisol | 0.05 g |
| Menthol | 0.06 g |
| Pure ethanol | 10.0 g |
| Active substance | 0.5 g |
| Citric acid | 0.7 g |
| Sec. sodiumphosphate × 2 H$_2$O | 0.3 g |
| Sodium cyclamate | 1.0 g |
| Glycerol | 15.0 g |
| Distilled water ad | 100.0 ml |

Preparation

The p-hydroxybenzoates, anisol and menthol are dissolved in ethanol (Solution I).

The buffer substances, active substance and sodium cyclamate are dissolved in distilled water and glycerol is added (Solution II). Solution I is stirred into Solution II and the mixture is topped up to the volume specified with distilled water. The finished drops solution is filtered through a suitable filter. The preparation and bottling of the drops solution must be carried out away from the light and under a protective gas.

EXAMPLE III

Suppositories containing 10 mg of 2-amino-6-dimethylamino-4,5,6,7-tetrahydro-benzthiazole-dihydrochloride

| 1 suppository contains: | |
|---|---|
| Active substance | 10.0 mg |
| Suppository mass (e.g. Witepsol W 45) | 1690.0 mg |

| 1 suppository contains: | |
|---|---|
| | 1700.0 mg |

Preparation

The finely powdered substance is stirred into the molten suppository mass, cooled to 40° C. with an immersion homogeniser. At 35° C. the mass is poured into slightly chilled moulds. Weight of suppository: 1.7 g

EXAMPLE IV

Ampoules containing 5 mg of 2-amino-6-dimethylamino-4,5,6,7-tetrahydro-benzthiazole-dihydrochloride

| 1 Ampoule contains: | |
|---|---|
| Active substance | 5.0 mg |
| Citric acid | 7.0 mg |
| Sec. sodium phosphate × 2H$_2$O | 3.0 mg |
| Sodium pyrosulphite | 1.0 mg |
| Distilled water ad. | 1.0 ml |

Preparation

The buffer substances, active substance and sodium pyrosulphite are successively dissolved in deionised water which has been cooled under CO$_2$ gas. The solution is made up to the volume specified with boiled water and filtered free from pyrogens. Bottling: in brown ampoules under protective gas Sterilization: 20 minutes at 120° C.

The preparation and transferring of the ampoule solution must be carried out in darkened rooms.

EXAMPLE V

Coated tablets containing 1 mg of 2-amino-6-dimethylamino-4,5,6,7-tetrahydro-benzthiazole-dihydrochloride

| 1 tablet core contains: | |
|---|---|
| Active substance | 1.0 mg |
| Lactose | 35.5 mg |
| Corn starch | 12.0 mg |
| Gelatine | 1.0 mg |
| Magnesium stearate | 0.5 mg |
| | 50.0 mg |

Preparation

Analogous to Example I

| Weight of core: | 50 mg |
|---|---|
| Punch: | 5 mm. convex |
| Weight of coated tablet: | 100 mg |

Obviously, instead of the compound mentioned, all the other compounds of general formula I may be incorporated as active substance in the Pharmaceutical Examples I to V, such as 2-amino-6-n-propylamino-4,5,6,7-tetrahydro-benzthiazole-dihydrochloride.

What is claimed is:

1. A tetrahydro-benzthiazole of the formula:

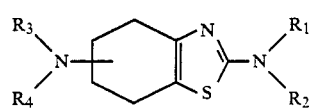

wherein

R$_1$ is a hydrogen atom, an alkyl group having 1 to 6 carbon atoms, an alkenyl or alkynyl group each having 3 to 6 carbon atoms, an alkanoyl group having 1 to 6 carbon atoms, a phenyl alkyl or phenyl alkanoyl group having 1 to 3 carbon atoms in the alkyl part, wherein the above mentioned phenyl nuclei may be substituted by 1 or 2 halogen atoms;

R$_2$ is a hydrogen atom or an alkyl group with 1 to 4 carbon atoms;

R$_3$ is a hydrogen atom, an alkyl group with 1 to 7 carbon atoms, a cycloalkyl group having 3 to 7 carbon atoms, an alkenyl or alkynyl group having 3 to 6 carbon atoms, an alkanoyl group having 1 to 7 carbon atoms, a phenyl alkyl or phenyl alkanoyl group having 1 to 3 carbon atoms in the alkyl part, whilst the phenyl nucleus may be substituted by fluorine, chlorine or bromine atoms; and, R$_4$ is a hydrogen atom, an alkyl group with 1 to 4 carbon atoms, an alkenyl or alkynyl group having 3 to 6 carbon atoms; or, R$_3$ and R$_4$ together with the nitrogen atom between them form a piperidino, hexamethyleneimino or morpholino group; or, an acid addition salt thereof.

2. A tetrahydro-benzthiazole of formula I, as claimed in claim 1, wherein the

group is in the 5 or 6-position.

3. A tetrahydro-benzthiazole of the formula:

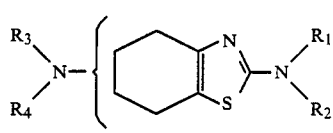

wherein

R$_1$ is a hydrogen atom, an alkyl group having 1 to 3 carbon atoms, an allyl, benzyl, 2-chloro-benzyl, 4-chloro-benzyl, 3,4-dichloro-benzyl or phenylethyl group;

R$_2$ is a hydrogen atom, a methyl or ethyl group;

R$_3$ is a hydrogen atom, an alkyl group with 1 to 6 carbon atoms, an allyl, propargyl, benzyl, chlorobenzyl, phenylethyl, cyclopentyl or cyclohexyl group; and, R$_4$ is a hydrogen atom, an alkyl group having 1 to 3 carbon atoms or an allyl group; or, R$_3$ and R$_4$ together with the nitrogen atom between them form a piperidino, hexamethyleneimino or morpholino group; or, a pharmaceutically acceptable acid addition salt thereof.

4. A tetrahydro-benzthiazole of formula Ia, as claimed in claim 3 wherein the

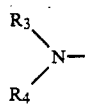

group is in the 6-position.

5. A tetrahydro-benzthiazole of formula Ia, as claimed in claim 3, wherein
R$_1$ and R$_2$ together with the nitrogen atom between them form an amino or allylamino group; and,
R$_3$ and R$_4$ together with the nitrogen atom between them form a dimethylamino, diethylamino, N-allyl-N-(4-chloro-benzyl)-amino, n- propylamino or group.

6. 2-Amino-6-dimethylamino-4,5,6,7-tetrahydro-benzthiazole, or a pharmaceutically acceptable acid addition salt thereof.

7. 2-Amino-6-n-propylamino-4,5,6,7-tetrahydro-benzthiazole, or a pharmaceutically acceptable acid addition salt thereof.

8. A pharmaceutical composition, suitable for the treatment of a disorder selected from the group consisting of high blood pressure, tachycardia, Parkinson's disease, Parkinsonism and schizophrenia, comprising a therapeutically effective amount of a compound according to claim 3 and a pharmaceutically acceptable carrier diluent.

9. A tetrahydrobenzthiazole of the formula

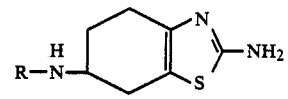

wherein R is an alkyl group with 1 to 7 carbon atoms, a cycloalkyl group having 3 to 7 carbon atoms, an alkenyl or alkynyl group having 3 to 6 carbon atoms, an alkanoyl group having 1 to 7 carbon atoms or a phenyl alkyl or phenyl alkanoyl group having 1 to 3 carbon atoms in the alkyl moiets, wherein the phenyl nucleus may be substituted by fluorine, chlorine or bromine atoms.

10. The compound of claim 9 wherein R is an alkyl group having 1 to 7 carbon atoms.

* * * * *